US012788701B2

(12) United States Patent
Ishida et al.

(10) Patent No.: US 12,788,701 B2
(45) Date of Patent: Nov. 10, 2026

(54) CERAMIDE GROWTH PROMOTING AGENT

(71) Applicant: TAKASAGO INTERNATIONAL CORPORATION, Tokyo (JP)

(72) Inventors: Kenya Ishida, Kanagawa (JP); Hisashi Mihara, Kanagawa (JP); Kyungho Park, Gangwon-do (KR); Yoshikazu Uchida, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 952 days.

(21) Appl. No.: 17/909,941

(22) PCT Filed: Mar. 8, 2021

(86) PCT No.: PCT/JP2021/009075
§ 371 (c)(1),
(2) Date: Sep. 7, 2022

(87) PCT Pub. No.: WO2021/182419
PCT Pub. Date: Sep. 16, 2021

(65) Prior Publication Data

US 2024/0197610 A1 Jun. 20, 2024

(30) Foreign Application Priority Data

Mar. 9, 2020 (JP) ................................. 2020-040142

(51) Int. Cl.
*A61K 8/68* (2006.01)
*A61G 19/00* (2006.01)
*A61Q 5/00* (2006.01)
*A61Q 19/00* (2006.01)

(52) U.S. Cl.
CPC ................ *A61K 8/68* (2013.01); *A61G 19/00* (2013.01); *A61Q 5/00* (2013.01)

(58) Field of Classification Search
CPC ............. A61K 8/68; A61Q 19/00; A61Q 5/00
See application file for complete search history.

(56) References Cited

U.S. PATENT DOCUMENTS 5,578,641 A 11/1996 Jackson et al.
6,355,232 B1 * 3/2002 Kaneko .................... A61K 8/68 424/401
6,497,888 B1 12/2002 Morancais et al.
2004/0009213 A1 1/2004 Skold
2005/0129722 A1 6/2005 Skold
2006/0210522 A1 9/2006 Ishida et al.
2009/0081139 A1 3/2009 Skold
2009/0226491 A1 9/2009 Skold
2022/0047491 A1 2/2022 Arakawa et al.

FOREIGN PATENT DOCUMENTS

CN 1784205 A 6/2006
CN 101909586 A 12/2010
EP 0 695 167 B1 12/1997
EP 0 920 852 A2 6/1999
EP 1 092 428 A1 4/2001
EP 1 633 313 B1 12/2016
JP 10-152428 A 6/1998
JP 2004-168763 A 6/2004
JP 2004-331595 A 11/2004
JP 2005-522463 A 7/2005
JP 2006176410 A * 7/2006 ............... A61K 8/00
JP 2007-308424 A 11/2007
JP 2012-92032 A 5/2012
JP 6602945 B1 11/2019
JP 2020-7270 A 1/2020
WO WO-2004098557 A1 * 11/2004 ........... A61K 8/0295
WO 2009/084200 A1 7/2009
WO WO-2009145299 A1 * 12/2009 .............. A61P 29/00
WO WO-2015136784 A1 * 9/2015 ............. A61K 8/375

OTHER PUBLICATIONS

Komorizono, M. et al. Effect of Human Ceramide Mixture (HC123) on Promoting Production of Ceramide. Aesthetic Dermatology 2016, 26, 269. (Year: 2016).*
Elias, P. M. Epidermal Lipids, Membranes, and Keratinization. Int J Dermatol 1981, 20, 1-19. (Year: 1981).*
Coderch, L., et al. Ceramides and Skin Function. Am J Clin Dermatol 2003, 4, 107-129. (Year: 2003).*
Blank, I. H. Factors which influence the water content of the stratum corneum. J Invest Dermatol 1952, 18, 433-440. (Year: 1952).*
Robson, K. J. et al. 6-Hydroxy-4-sphingenine in human epidermal ceramides. J. Lipid Res. 1994, 35, 2060-2068. (Year: 1994).*
Kováčik, A. et al. Effects of Ceramide and Dihydroceramide Stereochemistry at C-3 on the Phase Behavior and Permeability of Skin Lipid Membranes. Langmuir 2018, 34, 521-529. (Year: 2018).*
Di Marzio, L. et al. Increase of Skin-Ceramide Levels in Aged Subjects Following a Short-Term Topical Application of Bacterial Sphingomyelinase From *Streptococcus thermophilus* Int. J. Immunopathol. Pharmacol. 2008, 21, 137-143. (Year: 2008).*
Ishikawa, J. et al. Eucalyptus increases ceramide levels in keratinocytes and improves stratum corneum function. International Journal of Cosmetic Science 2012, 34, 17-22. First published: 2011 (Year: 2011).*

(Continued)

*Primary Examiner* — Jeffrey H Murray
*Assistant Examiner* — Kristen W Romero
(74) *Attorney, Agent, or Firm* — Sughrue Mion, PLLC

(57) ABSTRACT

A ceramide growth promoting agent includes ceramides represented by the general formula (1), in which, in the general formula (1), $R_1$ represents a monovalent hydrocarbon group having 13 to 21 carbon atoms which may have a hydroxyl group or a double bond, and Z represents an acyl group having 14 to 24 carbon atoms which may have a hydrogen atom, an acetyl group or a hydroxyl group:

(1)

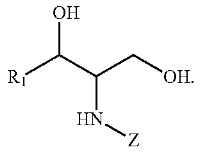

6 Claims, 5 Drawing Sheets

(56) References Cited

OTHER PUBLICATIONS

Takeda, S. et al. Strawberry seed extract and its major component, tiliroside, promote ceramide synthesis in the stratum corneum of human epidermal equivalents. PLoS ONE 2018, 13, e0205061. (Year: 2018).*
National Center for Biotechnology Information. "PubChem Compound Summary for CID 5283573, Ceramide NG" PubChem, https://pubchem.ncbi.nlm.nih.gov/compound/Ceramide-NG. Accessed Jan. 6, 2026. (Year: 2006).*
Office Action dated Mar. 29, 2024, issued by Chinese Patent Office in Chinese Patent Application No. 202180019737.6.
Communication issued on Mar. 15, 2024 by the European Patent Office for European Patent Application No. 21768041.2.
Office Action dated Jan. 26, 2025, issued by Chinese Patent Office in Chinese Patent Application No. 202180019737.6.
Wertz, et al., "Ceramides of pig epidermis: structure determination", 1983, Journal of Lipid Research, vol. 24, 759, 7 pages total.
Wertz, et al., "The Composition of the Ceramides from Human Stratum Corneum and from Comedones", 1985, Journal of Investigative Dermatology, vol. 84, 410, Issue 5, 3 pages total.
Komorizono, et al., "Effect of Human Ceramide Mixture (HC123) on Promoting Production of Ceramide", 2016, Aesthetic Dermatology, vol. 26, 269, 3 pages total.
Search Report (PCT/ISA/210) issued Apr. 27, 2021 by the International Searching Authority for International Application No. PCT/JP20217009075.
Written Opinion (PCT/ISA/237) issued Apr. 27, 2021 by the International Searching Authority for International Application No. PCT/JP20217009075.

* cited by examiner (a) ADD DMEM CONTAINING 1.2 mM CALCIUM, 10% FETAL BOVINE SERUM, 10 μg/mL INSULIN, 50 μg/mL ASCORBIC ACID,AND 0.4 μg/mL HYDROCORTISONE AND HAM F-12 LIQUID MEDIUM (2:1, V/V)

(b) ADD 1% CERAMIDE NDS SOLUTION: 15.9 μL, 79.6 μL, 397.7 μL, SEPARATELY ADD BLANK SOLUTION WITHOUT CERAMIDE: 79.6 μL (c) ADD DMEM LIQUID MEDIUM CONTAINING 1.2 mM CALCIUM, 10% FETAL BOVINE SERUM, 10 μg/mL INSULIN, 50 μg/mL ASCORBIC ACID, AND 0.4 μg/mL HYDROCORTISONE

CERAMIDE GROWTH PROMOTING AGENT

CROSS REFERENCE TO RELATED APPLICATIONS

This application is a National Stage of International Application No. PCT/JP2021/009075 filed on Mar. 8, 2021, claiming priority based on Japanese Application No. 2020-040142 filed on Mar. 9, 2020, the entire contents of all of which are incorporated by reference herein.

TECHNICAL FIELD

The present invention relates to a ceramide growth promoting agent whose conversion and growth into various ceramide species are promoted by application of a preparation containing dihydroceramides.

BACKGROUND ART

A skin has a very important function as a barrier membrane for avoiding biological, chemical, and physical invasiveness such as microorganisms, chemical substances, and ultraviolet rays from the outside and preventing loss of bioessential components such as moisture. A stratum corneum, which is located in the outermost layer of the epidermis and is approximately 20 μm thick, functions as the barrier membrane. Intercellular lipids connect keratinocytes, which are stacked like bricks, together like a mortar to form a strong barrier membrane. Ceramide is known to construct a lipid barrier as a key component in this keratinous intercellular lipid, and play an important role in keeping the skin soft and fresh (Non-Patent Literature 1 and Non-Patent Literature 2).

In recent years, it has become clear that the content of ceramide in these keratinous intercellular lipids in the skin of patients with rough skin, dry skin, and atopic dermatitis is significantly lower than that in the skin of healthy people. Attempts have been made to improve the skin barrier function and the moisturizing function by applying and supplementing ceramides to rough skin and damaged skin.

On the other hand, attempts have been made to improve the skin barrier function and the moisturizing function by promoting a ceramide production mechanism using an extract of *Eucalyptus robusta* Smith, *Typha orientalis* Presl, *Scoparia dulcis* L., *Syringa oblata* Lindl., or the like as an active ingredient (Patent Literature 1).

FIG. 1 shows an abbreviation for ceramide. Ceramide is classified into 12 types according to a combination of a sphingosine base and a long-chain fatty acid constituting an amide side chain, and may be abbreviated in the present specification.

Ceramide EOSs (FIG. 1: CER [EOS]) may be referred to as ceramide 1, ceramide NSs (FIG. 1: CER [NS]) may be referred to as ceramide 2, and ceramide NDSs (FIG. 1: CER [NDS]) may be referred to as dihydroceramide 2.

Here, as a technique of related art, a report of an effect of promoting ceramide production by applying a mixture of ceramide 1, ceramide 2, and ceramide 3 (Non-Patent Literature 3), and a delivery system using a preparation composed of water, a fatty acid, cholesterol, and ceramide/phospholipid have been proposed (Patent Literature 2).

CITATION LIST

Patent Literature

Patent Literature 1: JP-A-H10-152428
Patent Literature 2: JP-T-2005-522463

Non-Patent Literature

Non-Patent Literature 1: Downing D. T., et al., J. Lipid. Res., 24, 759 (1983)
Non-Patent Literature 2: Downing D. T., et al., J. Invest. Dermat., 84,410 (1985)
Non-Patent Literature 3: M. Komorizono., et al., Aesthetic dermatology, 26 (2), 269 (2016)

SUMMARY OF INVENTION

Technical Problem

However, the method for supplementing ceramide from the outside described in Patent Literature 1 limits the kind of ceramide, attempts to promote ceramide production from the inside have various problems such as the need to reach deep into the epidermis (for example, into a nucleated basal layer, spinous layer, and granular layer in the case of serine paimitoyltransferase) where a conversion enzyme on which a production promoter acts is present, and further, the individual differences in production capacity. Therefore, more effective preparation development has been desired.

In the technique described in Non-Patent Literature 3, an expensive mixture of ceramide 1, ceramide 2, and ceramide 3 is essential. In the technique described in Patent Literature 2, a fatty acid is essential as a system constituent component, and specific examples of ceramides include expensive ceramide 1, ceramide 3, ceramide 611, and phytosphingosine which is a precursor of ceramide NP, as in Non-Patent Literature 3. As described above, the effect of using ceramides alone, and the effect of using dihydroceramide 2 (ceramide NDS) alone, and the effect of a system that does not require a fatty acid have not been known at all.

The present invention has been made under such circumstances, and an object of the present invention is to provide a preparation and technology capable of not only supplementing ceramides from the outside but also enabling the growth of various ceramide species in an external preparation for skin. Ceramide growth in the present disclosure means promoting biosynthesis ability and/or synthesis ability of the epidermal stratum corneum ceramide.

Solution to Problem

As a result of intensive studies in view of the above circumstances, the present inventors have found that application of specific ceramides can not only supplement ceramides from the outside but also enable the growth of various ceramide species, and have completed the present invention.

That is, the present invention includes the following contents.

[1] A ceramide growth promoting agent including ceramides represented by the following general formula (1).

[Chem. 1]

(1)

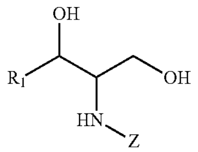

(In the formula, $R_1$ represents a monovalent hydrocarbon group having 13 to 21 carbon atoms which may have a hydroxyl group or a double bond, and Z represents an acyl group having 14 to 24 carbon atoms which may have a hydrogen atom, an acetyl group or a hydroxyl group.)

[2] The ceramide growth promoting agent according to [1], in which the ceramides represented by the general formula (1) are ceramides represented by the following general formula (2).

[Chem. 2]

(2)

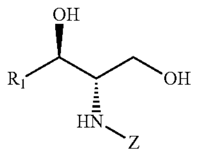

(In the formula, R j represents a monovalent hydrocarbon group having 13 to 21 carbon atoms which may have a hydroxyl group or a carbon-carbon double bond, and Z represents an acyl group having 14 to 24 carbon atoms which may have a hydrogen atom, an acetyl group or a hydroxyl group.

[3] The ceramide growth promoting agent according to [1] or [2], in which $R_1$ in the general formula (1) or the general formula (2) is a monovalent saturated hydrocarbon group having 13 to 21 carbon atoms.

[4] The ceramide growth promoting agent according to any one of [1] to [3], further including any one or more of cholesterol, phytosterol, polyglycerin fatty acid ester, and polyhydric alcohol.

[5] The ceramide growth promoting agent according to any one of [1] to [4], further including water and any one or more of cholesterol, decaglycerol monostearate, butylene glycol, and glycerin, in which $R_1$ in the general formula (1) or the general formula (2) is a monovalent saturated hydrocarbon group having 13 to 21 carbon atoms.

[6] The ceramide growth promoting agent according to any one of [1] to [5], in which ceramide to be grown is ceramides represented by the following general formula (3).

[Chem. 3]

(3)

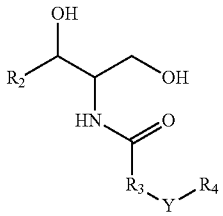

(In the formula, $R_2$ represents a monovalent hydrocarbon group having 13 to 21 carbon atoms which may have a carbon-carbon double bond and/or a hydroxyl group, $R_3$ represents a divalent saturated hydrocarbon group having 13 to 31 carbon atoms which may have a hydroxyl group, Y represents a hydrogen atom or an O-acyl bond via a hydroxyl group, $R_4$ does not exist in a case where Y is a hydrogen atom, and $R_4$ represents a monovalent hydrocarbon group having 15 to 25 carbon atoms which may have a carbon-carbon double bond in a case where Y is an O-acyl bond via a hydroxyl group.)

[7] The ceramide growth promoting agent according to any one of [1] to [5], in which ceramide to be grown is ceramides represented by the following general formula (4).

[Chem. 4]

(4)

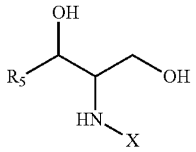

(In the formula, $R_5$ represents a monovalent hydrocarbon group having 13 to 21 carbon atoms which has a carbon-carbon double bond, and X represents an acyl group having 14 to 24 carbon atoms.

[8] The ceramide growth promoting agent according to any one of [1] to [7], in which a diameter of dispersed particles is 0.45 μm or less.

[9] The ceramide growth promoting agent according to any one of [1] to [8], which is substantially free of a fatty acid and/or a phospholipid and includes only a nonionic component.

[10] A skin cosmetic, a skin protective agent, a hair composition, a lip care preparation, a skin cleanser, or a bath agent, including the ceramide growth promoting agent according to any one of [1] to [9].

[11] A method for growing and/or supplementing various ceramide species in a skin stratum corneum by applying the ceramide growth promoting agent according to any one of [1] to [9].

Advantageous Effects of Invention

As described above, the ceramide growth promoting agent of the present invention containing ceramides having a specific structure can increase ceramides in an appropriate balance by promoting the growth of various ceramides. Furthermore, since the preparation is excellent in stability, safety, and feeling of use and can be optionally diluted in a wide range of skin/hair (scalp) preparations, the use as a raw material for cosmetics and medicines is remarkably expanded.

DESCRIPTION OF EMBODIMENTS

Figure 1:
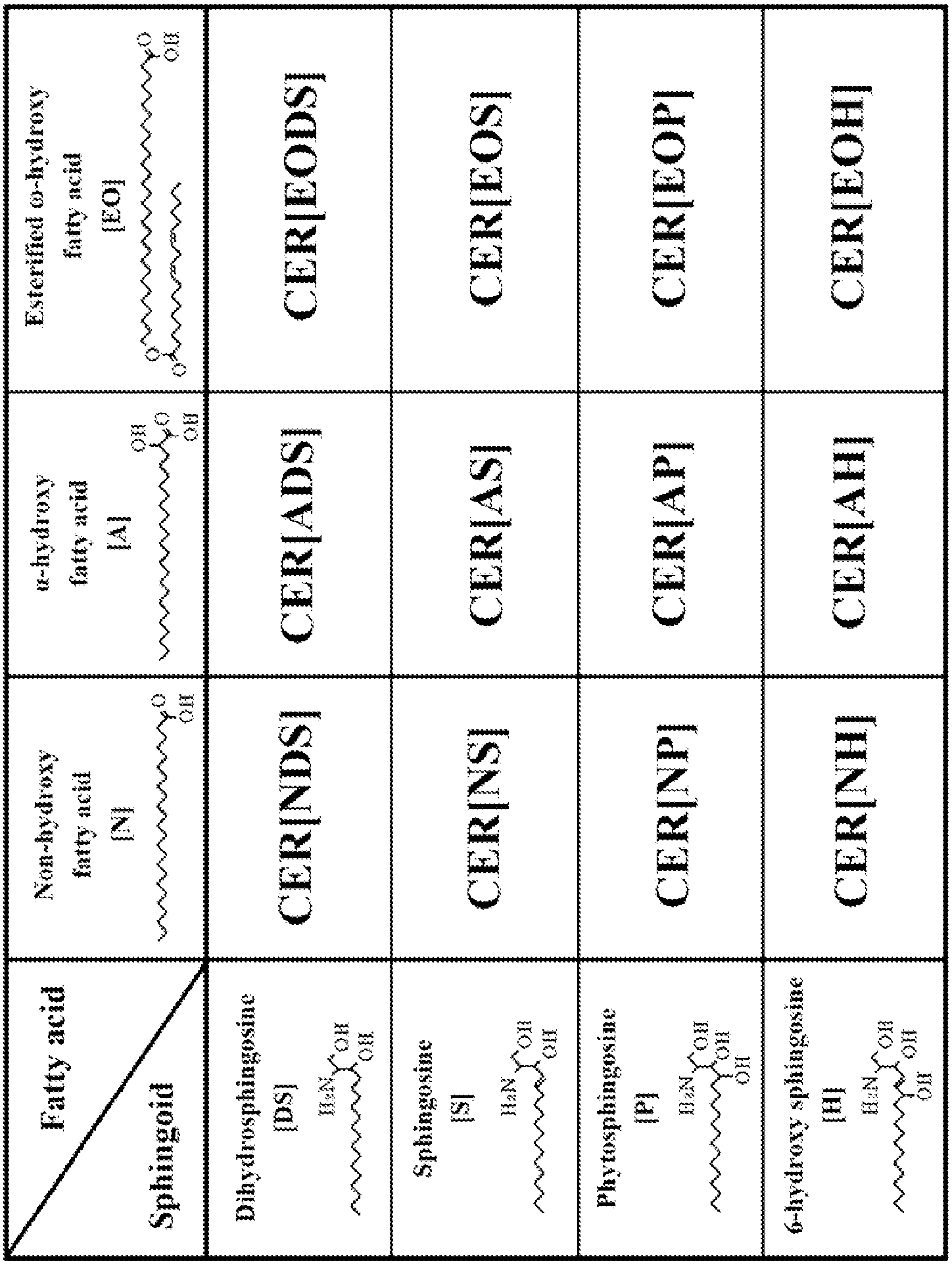
FIG. 1 is a diagram showing an abbreviation for ceramide.

Ceramides used in the present invention are known compounds represented by the following formula (1).

[Chem. 5]

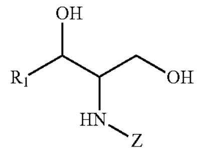

(1)

(In the formula, $R_1$ represents a monovalent hydrocarbon group having 13 to 21 carbon atoms which may have a hydroxyl group or a double bond, and Z represents an acyl group having 14 to 24 carbon atoms which may have a hydrogen atom, an acetyl group or a hydroxyl group.)

The compounds of the general formula (1) can be obtained from a mammalian extract of human or porcine skin, cow brain, red blood cells, or the like, and a plant extract of soybean, wheat, or the like. A synthetic product obtained by a known production method is suitably used in terms of purity.

Specific examples of the compounds represented by the general formula (1) include 2-tetradecanoylaminooctadecane-1,3-diol, 2-hexadecanoylaminooctadecane-1,3-diol, 2-octadecanoylaminooctadecane-1,3-diol, 2-eicosanoylaminooctadecane-1,3-diol, 2-oleoylaminooctadecane-1,3-diol, 2-linoleoylaminooctadecane-1,3-diol, 2-(2-hydroxyhexadecanoyl)aminooctadecane-1,3-diol, 2-(3-hydroxyhexadecanoyl)aminooctadecane-1,3-diol, 2-tetradecanoylaminohexadecane-1,3-diol, 2-hexadecanoylaminohexadecane-1,3-diol, 2-octadecanoylaminohexadecane-1,3-diol, 2-eicosanoylaminohexadecane-1,3-diol, 2-oleoylaminohexadecane-1,3-diol, 2-linoleoylaminohexadecane-1,3-diol, 2-(2-hydroxyhexadecanoyl)aminohexadecane-1,3-diol, 2-octadecanoylaminooctadecane-1,3,4-triol, and the like. These can be used alone or in combination of two or more kinds thereof.

Further, as the ceramides used in the present invention, optically active natural ceramides represented by the following general formula (2) are particularly preferably used.

[Chem. 6]

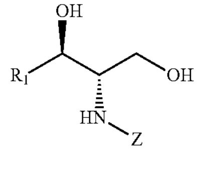

(2)

(In the formula, $R_1$ represents a monovalent hydrocarbon group having 13 to 21 carbon atoms which may have a hydroxyl group or a carbon-carbon double bond, and Z represents an acyl group having 14 to 24 carbon atoms which may have a hydrogen atom, an acetyl group or a hydroxyl group.)

Specific examples of the compounds represented by the general formula (2) include (2S,3R)-2-tetradecanoylaminooctadecane-1,3-diol, (2S,3R)-2-hexadecanoylaminooctadecane-1,3-diol, (2S,3R)-2-octadecanoylaminooctadecane-1,3-diol, (2S,3R)-2-nonadecanoylaminooctadecane-1,3-diol, (2S,3R)-2-eicosanoylaminooctadecane-1,3-diol, (2S,3R)-2-oleoylaminooctadecane-1,3-diol, (2S,3R)-2-reoylaminooctadecane-1,3-diol, (2S,3R)-2-(2-hydroxyhexadecanoyl)aminooctadecane-1,3-diol, (2S,3R)-2-(3-hydroxyhexadecanoyl)aminooctadecane-1,3-diol, (2S,3R)-2-tetradecanoylaminohexadecane-1,3-diol, (2S,3R)-2-hexadecanoylaminohexadecane-1,3-diol, (2S,3R)-2-octadecanoylaminohexadecane-1,3-diol, (2S,3R)-2-nonadecanoylaminohexadecane-1,3-diol, (2S,3R)-2-eicosanoylaminohexadecane-1,3-diol, (2S,3R)-2-oleoylaminohexadecane-1,3-diol, (2S,3R)-2-linoylaminohexadecane-1,3-diol, (2S,3R)-2-(2-hydroxyhexadecanoyl)aminohexadecane-1,3-diol, and (2S,3S,4R)-2-octadecanoylaminooctadecane-1,3,4-triol. These can be used alone or in combination of two or more kinds thereof.

$R_1$ in the general formula (1) or general formula (2) is particularly preferably a monovalent saturated hydrocarbon group having 13 to 21 carbon atoms. Compounds in which $R_1$ in the general formula (1) or the general formula (2) is a monovalent saturated hydrocarbon group having 13 to 21 carbon atoms are classified into dihydroceramide (ceramide NDS) (CER (NDS) in FIG. 1).

The total content of these ceramides in the ceramide growth promoting agent of the present invention is preferably 0.001 mass % to 10 mass %, more preferably 0.01 mass % to 5 mass %, based on the total amount of the ceramide growth promoting agent.

The ceramide growth promoting agent of the present invention preferably further includes one or more of sterols such as cholesterol and phytosterol, polyglycerin fatty acid esters, and polyhydric alcohols, in addition to the ceramides described above. By using these components in combination, the component of the ceramide growth promoting agent can be suitably adjusted.

More specific examples of the sterols include cholesterol, cambersterol, stigmasterol, and sitosterol, and cholesterol, which is a natural component constituting the stratum corneum, is particularly preferable. When the sterols are used in combination, the content thereof is preferably 20 mass % to 150 mass % with respect to the ceramides.

The polyglyceric acid fatty acid esters preferably have a hydrophile-lipophile balance (H.L.B.) of 10 or more. A polyglycerin group of fatty acid ester of polyglycerin preferably has a degree of polymerization of 5 or more, particularly preferably 8 to 12. In addition, a fatty acid residue is preferably a fatty acid residue having 12 to 24 carbon atoms, such as a lauric acid residue, a myristic acid residue, a palmitic acid residue, a stearic acid residue, a behenic acid residue, an isostearic acid residue, and an oleic acid residue. The number of fatty acid residues is preferably larger than the number of liberate aquatic groups. Preferably, 5 to 20 liberate hydroxyl groups with respect to the number of fatty acid residues are present. Specific preferred examples thereof include decaglycerin monomillistate (HLB14), pentaglycerin monostearate (HLB11), decaglycerin monostearate (HLB13.5), pentaglycerin monoisostearate (HLB11), and decaglycerin monoolate (HLB13). These components may be contained alone or in combination of two or more kinds thereof.

These components act as a hydrophilic surfactant. Fatty acid esters of polyglycerin are easy to form a liquid crystal structure together with poorly water-soluble components and alcohols. When the liquid crystal structure is formed in at least a part of a matrix, the ceramide component becomes present on the skin as a matrix that is easy to undergo transdermal absorption.

Preferred examples of the treatment method for easily producing a liquid crystal include: 1) heating and compatibilizing a matrix constituent component containing poorly soluble ceramides and alcohols, 2) diluting the matrix constituent component with a non-aqueous component, other than the matrix constituent component, containing a fatty acid ester of polyglycerin as a surfactant and a polyhydric alcohol, which has been previously heated and compatibilized, and 3) adding a previously heated aqueous component to the diluted product, followed by cooling.

The amount of the fatty acid ester of polyglycerin is preferably 2 to 20 times by mass with respect to the total amount of ceramides.

Examples of the polyhydric alcohols include 1,3-butanediol, dipropylene glycol, glycerin, diglycerin, isoprene glycol, 1,2-pentanediol, and 1,2-hexylene glycol. These can be used alone or in combination of two or more kinds thereof. In particular, 1,3-butanediol and glycerin are preferably used.

The content of the polyhydric alcohols is not particularly limited, but use of the polyhydric alcohols in an amount of 10 to 50 times the amount of the ceramides is preferable as a stable dispersion preparation of the ceramides in water.

The ceramide growth promoting agent of the present invention can include optional components commonly used in skin and hair external preparations in a state of being divided into a phase of a non-aqueous component and a phase of water, as long as the effects of the present invention are not impaired. Examples of such optional components include hydrocarbons such as squalane, liquid paraffin, light liquid isoparaffin, hcavy liquid isoparaffin, microcrystalline wax, and solid paraffin; silicones such as dimethicone, phenylmethicone, cyclomethicone, amodimethicone, and polyether-modified silicon; esters such as jojoba oil, carnauba wax, Japan wax, beeswax, spermaceti, octyldodecyl oleate, isopropyl myristate, dineopentyl glycol diisostearate, and diisostearyl malate; fatty acids such as stearic acid, lauric acid, myristic acid, palmitic acid, isostearic acid, isopalmitic acid, behenic acid, and oleic acid; triglycerides such as castor oil, coconut oil, hydrogenated coconut oil, camellia oil, wheat germ oil, triglyceride isostearate, triglyceride isooctanoate, and olive oil; polyhydric alcohols such as 1,3-butanediol, glycerin, diglycerin, dipropylene glycol, polyethylene glycol, 1,2-pentanediol, 1,2-hexylene glycol, and isoprene glycol; organic powders such as crystalline cellulose, crosslinked methylpolysiloxane, polyethylene powder, and acrylic resin powder; powders, which may be surface-treated, such as talc, mica, sericite, magnesium carbonate, calcium carbonate, titanium dioxide, iron oxide, Prussian blue, ultramarine, titanium mica, titanium sericite, and silica; thickeners such as an acrylic acid-alkyl methacrylate copolymer and/or a salt thereof, a carboxyvinyl polymer and/or a salt thereof, xanthan gum, or hydroxypropyl cellulose; active ingredients such as vitamins such as retinol, retinoic acid, tocopherol, riboflavin, pyridoxin, ascorbic acid, and ascorbic acid phosphate ester salts, and steroids such as estradiol, ethynylestradiol, and estriol; preservatives such as phenoxyethanol, parabens, hibitane gluconate, benzalkonium chloride; and UV absorbents such as dimethylaminobenzoic acid esters, cinnamic acid esters, and benzophenones. These may be used alone or in combination of two or more kinds thereof.

However, the pH of fatty acids such as stearic acid, lauric acid, myristic acid, palmitic acid, isostearic acid, isopalmitic acid, behenic acid, and oleic acid need to be adjusted with an alkaline agent, and neutralization with an alkali salt such as sodium or potassium may cause skin irritation. Therefore, except for being intentionally used as an active ingredient of the skin/hair cleanser, the fatty acids are not preferably used, and it is preferable that fatty acids are not substantially contained. In addition, it is preferable that phospholipids such as lecithin are not substantially contained from the viewpoint of the risk that the surfactant action or the like thereof affects the essence of the present invention. From the viewpoint of avoiding the risk of affecting the pH of the product, the ceramide growth promoting agent of the present invention preferably includes only a nonionic component. The nonionic component mainly means a nonionic surfactant, and examples thereof include fatty acid esters of polyglycerin.

The ceramide growth promoting agent of the present invention can be applied to any preparation for external medicines for skin/hair. Examples of the preparation containing the ceramide growth promoting agent of the present invention include a skin cosmetic, a skin protective agent, a hair composition, a lip care preparation, a skin cleanser, and a bath agent.

In the ceramide growth promoting agent of the present invention, a diameter of dispersed particles is preferably 0.45 μm or less. When a particle diameter of the ceramides falls within such range, the ceramides can pass through many treatment membranes in preparation development, which is preferable. In order to set the particle diameter of the ceramides within the above range, for example, the ceramide growth promoting agent preferably includes a polyglycerin fatty acid ester.

In related art, there has been known that the barrier function and the moisturizing function of the skin are improved by applying a preparation containing ceramide as an external preparation, but the ceramide growth promoting agent of the present invention has an effect of being converted into various ceramide species and/or an effect of promoting the growth effect of various ceramide species particularly by containing a dihydroceramide having a dihydrosphingosine skeleton. Such knowledge has not been known at all.

According to the ceramide growth promoting agent of the present invention, preferably, ceramides (ceramide EOSs) represented by the following general formula (3) and ceramides (ceramide NSs) represented by the following general formula (4) are grown.

[Chem. 7]

(3)

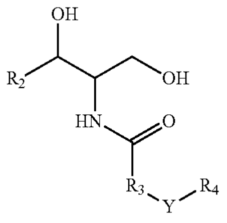

(In the formula, $R_2$ represents a monovalent hydrocarbon group having 13 to 21 carbon atoms which may have a carbon-carbon double bond and/or a hydroxyl group, R represents a divalent saturated hydrocarbon group having 13 to 31 carbon atoms which may have a hydroxyl group, Y represents a hydrogen atom or an O-acyl bond via a hydroxyl group, $R_1$ does not exist in a case where Y is a hydrogen atom, and $R_4$ represents a monovalent hydrocarbon group having 15 to 25 carbon atoms which may have a carbon-carbon double bond in a case where Y is an O-acyl bond via a hydroxyl group.)

[Chem. 8]

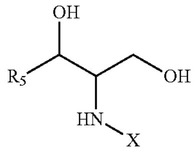

(4)

(In the formula, $R_5$ represents a monovalent hydrocarbon group having 13 to 21 carbon atoms which has a carbon-carbon double bond, and X represents an acyl group having 14 to 24 carbon atoms.)

EXAMPLE

Next, the present invention will be described in more detail with reference to Examples and Test Examples, but the present invention is not limited to these Examples.

In this example, as ceramide NDS, one manufactured by Takasago International Co., Ltd. was used, and as ceramides other than the ceramide NDS, those manufactured by Avanti Polar Lipids Co., Ltd. were used.

Example 1

A ceramide dispersion preparation (ceramide composition) including (2S,3R)-2-octadecanoylaminooctadecane-1,3-diol (dihydroceramide 2=ceramide NDS) having an optical purity and a chemical purity of 95% or more was prepared according to the following formulation.

A lipid component composed of a component (a) was uniformly dissolved at about 120° C., subsequently, a component (b) was added at the same temperature to be dissolved transparently, and then a component (c) heated to 80 to 90° C. in advance was gradually added dropwise.

Component (a)

Ceramide NDS: 1.00 parts by mass

Cholesterol: 0.75 parts by mass

Component (b)

Decaglyceryl monomyristate: 4.50 parts by mass 1,3-butylene glycol: 20.00 parts by mass Glycerin: 10.00 parts by mass Component (c)

Water: 63.75 parts by mass

Comparative Example 1

A ceramide-free preparation (Placebo=Blk) was prepared with the same formulation as in Example 1 except without ceramide NDS.

Example 2

A ceramide preparation (ceramide composition) was prepared using polyoxyethylene hydrogenated castor oil (HCO60) instead of decaglyceryl monomyristate of Example 1.

Example 3

A ceramide preparation (ceramide composition) was prepared using polyglyceryl (13) polyoxybutylene (14) stearyl ether instead of decaglyceryl monomyristate of Example 1.

Comparative Example 2

A ceramide preparation (ceramide composition) was prepared using ceramide NP instead of ceramide NDS of Example 1.

(Test Example 1) Quantification of Ceramide Permeation Amount by Dilution of Ceramide Growth Promoting Agent and Filter Paper Filtration When the produced ceramide preparation was subjected to a cell culture test, the amount of ceramide was quantified before and after filtration of a diluted solution of phosphate buffered saline of the ceramide preparation with a syringe filter.

Preparation of Internal Standard Solution:

As an internal standard solution, about 0.40 g of ethyl stearate (special grade of Nakarai standard, manufactured by Nacalai Tesque, Inc.) was precisely weighed and dissolved by adding tetrahydrofuran to prepare a solution having an accurate volume of 20 ml.

Preparation of Calibration Curve:

A calibration curve was prepared by the following method.

About 50 g of (2S,3R)-2-octadecanoylaminooctadecane-1,3-diol standard product (this product was recrystallized three times with ethanol and dried, and no related substances were observed) was precisely weighed and diluted up to 50 ml with tetrahydrofuran to prepare a standard stock solution. 1 ml, 2 mi and 3 ml of the standard stock solution were accurately weighed, 1 ml of the internal standard solution was added accurately, and then methanol was added to make 10 ml, which were used as a standard solution. Each 20 µl of these solutions was tested by liquid chromatography under the following operation conditions, and a ratio of a peak area of (2S,3R)-2-octadecanoylaminooctadecane-1,3-diol to a peak area of the internal standard substance was determined from the obtained chromatogram. This ratio was plotted on a vertical axis, and a ratio of the mass of the (2S,3R)-2-octadecanoylaminooctadecane-1,3-diol standard product to the mass of the internal standard substance was plotted on a horizontal axis, thereby preparing a calibration curve.

Quantification of Ceramide Permeation Amount

Each ceramide preparation of Examples 1 to 3 was diluted 10 times with a phosphate buffered saline. The following operations were performed on the diluted solution before filtration and the diluted solution obtained by filtering the diluted solution with a syringe filter (manufactured by Millipore, Myrex-HV filter, 0.45 µm). 10.0 mL of the diluted solution was weighed, and the solvent was removed from the diluted solution by a rotary evaporator at 60° C. over 15 minutes at 200 to 20 mmHG. To the dried and solidified sample, 5 ml of tetrahydrofuran was added, and the mixture was irradiated with ultrasonic waves, followed by heating to 60° C. to obtain a suspension. The suspension was diluted with tetrahydrofuran to 10 mi, 2 ml of the supernatant was weighed, 2 mi of an internal standard solution (internal standard substance: ethyl stearate) were added thereto, and the mixture was diluted with methanol (manufactured by Wako Pure Chemical Industries, Ltd., for liquid chromatography) to 10 ml to prepare a test solution. For 20 μl of the test solution, a test was performed by a liquid chromatography method, and a ratio of a peak area of (2S,3R)-2-octadecanoylaminooctadecane-1,3-diol to a peak area of the internal standard substance was determined. Further, the mass ratio was determined from the calibration curve prepared in advance, and the amount was quantified by the following calculation formula.

Amount (mg) of (2S,3R)-2-octadecanoylamino-octadecane-1,3-diol=$A$×Mass ratio determined from calibration curve Calculation Formula:

A: amount (mg) of internal standard substance (ethyl stearate) in 1 ml of internal standard solution The measurement by the high-performance liquid chromatograph was performed under the following conditions. Detector: ultraviolet absorption photometer (measurement wavelength: 210 nm), column: Inertsil ODS-3 (manufactured by Nacalai Tesque, Inc., 4.6 mm×25 cm), column temperature: 40° C., mobile phase: methanol, flow rate: 1.0 ml/min.

The ceramide permeation amount (transmittance) after filtration is shown in Table 1 below.

TABLE 1

| | |
|---|---|
| Example 1 | 99.5% |
| Example 2 | 68.5% |
| Example 3 | 75.7% |

From the above results, it was found that a ceramide growth promoting agent having a fine particle size can be prepared by containing decaglyceryl monomyristate.

(Test Example 2) Ceramide Growth Test

<Human Keratinocytes Culture and preparation Addition Test>

Experiments were conducted using undifferentiated and late differentiated cultured human keratinocytes (KCs). Human keratinocytes were cultured in a serum-free KC growth medium containing 0.07 mM calcium, and collected to be undifferentiated cells when KCs occupied up to about 60% to 70% of the total area of the culture petri dish (about 60% to 70% confluence). KCs were cultured in a serum-free KC growth medium containing 0.07 mM of calcium, and the medium was replaced with DMEM containing 10% fetal bovine serum containing 1.2 mM of calcium, 10 μg/mL insulin, 0.4 μg/mL hydrocortisone, and 50 μg/mL of vitamin C and Ham's F-12 (2:1, v/v) when KCs occupied up to about 70% to 80% of the total area of the culture petri dish (about 70% to 80% confluence), followed by culturing for 8 days. Next, cells cultured for 3 days in a DMEM medium containing 10% fetal bovine serum containing 1.2 mM of calcium, 10 μg/mL insulin, 0.4 μg/mL hydrocortisone, and 50 μg/mL of vitamin C were used as late differentiated cultured human keratinocytes (LDKs).

Figure 2:
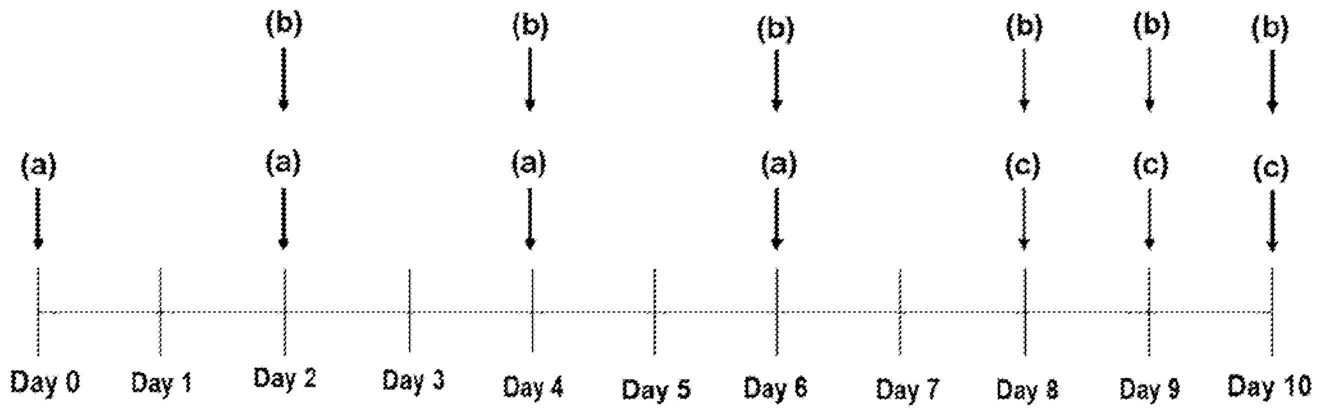
FIG. 2 is a diagram showing a culture and a preparation addition test.

Culturing was carried out from Day 0 to 10 for 10 days in the process as shown in FIG. 2, and various ceramides were quantified on the final day. From the second day of culture to the fourth, sixth, eighth, ninth, and tenth days, the ceramide preparation (I % ceramide NDS solution) prepared in Example 1 was diluted with a medium, filtered with a filter paper having a pore size of 0.45 μm, and 15.9 μL, 79.6 μL, and 397.7 μL (=10 μM, 50 μM, 250 μM) thereof were added, separately. In addition, 79.6 μL of a Blk solution not containing ceramide prepared in Comparative Example 1 was added, followed by culturing.

<Ceramide Growth Test>

100 μg of each of the culture solutions prepared above and 100 μmol of an internal standard substance mixture (C17 (carbon number 17)-ceramide NS=N-octadecanoylamino-C17 sphingosine, C17-sphingosine, C17-dihydrosphingosine) were added to a mixed solution of a 0.1 N HCl aqueous solution:chloroform:methanol (volume ratio 1:2:1) and stirred, and then the organic phase of the lower layer was dried in vacuo, and the extraction drying operation was repeated twice. The obtained residue was dissolved in 200 μl of a methanol/acetonitrile equivalent mixture, and analyzed by the following liquid chromatography tandem mass spectrometry (LC-ESI-MS/MS) system (API 3200 QTRAP mass, ABCIEX).

Optimization of analysis accuracy: A mixture of each ceramide standard substance (ceramide NDS of sphingosine base having 14 to 26 carbon atoms and ceramide NS) was used, and all ion source parameters and ionization conditions were adjusted to optimize the analysis accuracy.

10 μL of the extracted sample was analyzed by HPLC (HTS HPLC system manufactured by Shiseido Co., Ltd.) with a reverse phase KINTEX C18 column (2.1×50 mm, ID=2.6 μm). The column was previously equilibrated with a solvent A (MeOH: 0.05% formic acid aqueous solution: 80:20), the lipid was dissolved in a solvent B (2-propanol: 0.05% formic acid methanol solution: 99:1), and a mass spectrum was detected in a positive mode by electrospray ionization with a gradient applied at a flow rate of 0.3 ml/min. 5 mM ammonium formate was added to both of the solvents A and B to promote buffering and sensitivity improvement.

In MS/MS, precursor ions m/z[M+H]+ of various ceramide components were captured in the first stage, collision and decomposition were performed in the second stage, and product ions m/z obtained in the decomposition in the third stage were detected.

Quantification of various ceramide species was performed using Analyst 1.5.1 (manufactured by Applied Biosystems) by comparison with the calibration curve obtained from the internal standard substance, and was calculated as the ceramide amount pmol/g in the stratum corneum.

The monitoring parameters of various ceramides are shown in Table 2.

TABLE 2

| Ceramide species | Precursor ion | Product ion | Collision energy (V) |
|---|---|---|---|
| Ceramide EOSs | | | |
| C18:2n-6/C30wh:1/d18:1 | 1011.0 | 264.3, 993.0 | 39, 17 |
| C18:2n-6/C30wh:0/d18:1 | 1013.0 | 264.3, 995.0 | 39, 17 |
| C18:2n-6/C32wh:1/d18:1 | 1039.0 | 264.3, 1019.0 | 39, 17 |
| C18:2n-6/C32wh:0/d18:1 | 1041.0 | 264.3, 1021.0 | 39, 17 |
| Ceramide NSs | | | |
| C18:0/dl17:1 (Internal standard) | 552.2 | 250.3 | 35 |
| C14:0/d18:1 | 510.2 | 264.3 | 35 |
| C16:0/d18:1 | 538.3 | 264.3 | 35 |
| C18:0/d18:1 | 566.3 | 264.3 | 36 |

TABLE 2-continued

| Ceramide species | Precursor ion | Product ion | Collision energy (V) |
|---|---|---|---|
| C20:0/d18:1 | 594.4 | 264.3 | 37 |
| C22:0/d18:1 | 622.5 | 264.3 | 37 |
| C24:1/d18:1 | 648.6 | 264.3 | 40 |
| C24:0/d18:1 | 650.6 | 264.3 | 41 |
| C26:1/d18:1 | 676.7 | 264.3 | 43 |
| C26:0/d18:1 | 678.7 | 264.3 | 43 |
| Ceramide NDSs | | | |
| C14:0/d18:0 | 512.2 | 284.3 | 35 |
| C16:0/d18:0 | 540.3 | 284.3 | 35 |
| C18:0/d18:0 | 568.3 | 284.3 | 36 |
| C20:0/d18:0 | 596.4 | 284.3 | 37 |
| C22:0/d18:0 | 624.5 | 284.3 | 37 |
| C24:1/d18:0 | 650.6 | 284.3 | 40 |
| C24:0/d18:0 | 652.6 | 284.3 | 41 |
| C26:1/d18:0 | 678.7 | 284.3 | 43 |
| C26:0/d18:0 | 680.7 | 284.3 | 43 |
| C17-sphingosine (Internal standard) | 286.2 | 268.2 | 17 |
| Sphingosine (C18) | 300.2 | 282.2 | 17 |
| C17-dihydrosphingosine (Internal standard) | 288.2 | 60.2 | 35 |
| Dihydrosphingosine (C18) | 302.2 | 60.1 | 35 |

(Test Result 2-1)

Figure 3:
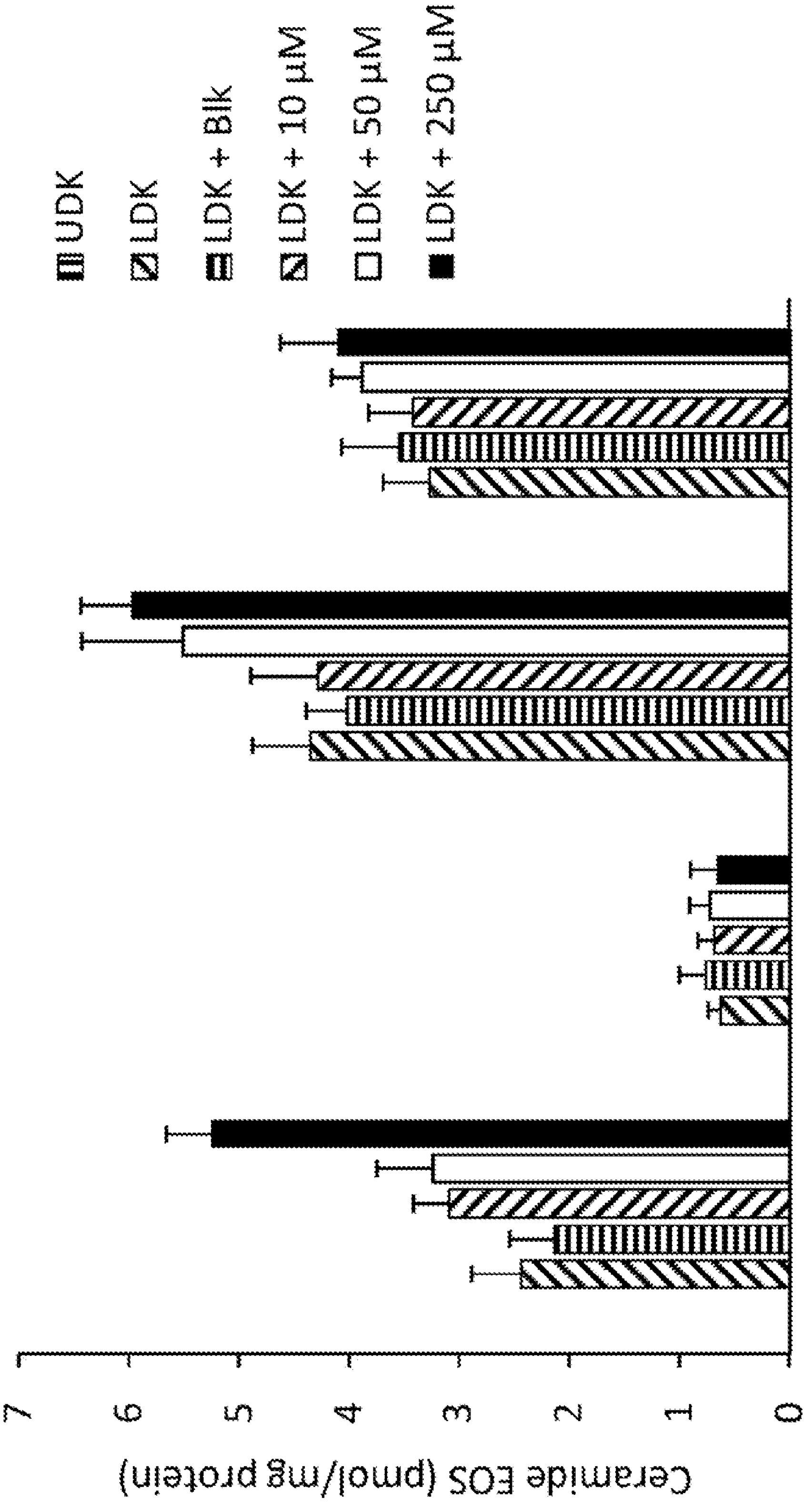
FIG. 3 is a diagram showing quantification results of ceramide EOSs.

The quantification results of ceramide EOSs are shown in FIG. 3.

As is clear from FIG. 3, it was confirmed that in the culture system to which ceramide NDS was added, ceramide EOSs having a ω-hydroxy acid amide bond having 30 and 32 carbon atoms which esterified with linoleic acid at a ω-position significantly increased. Note that # indicates a significant difference $p<0.01$ with respect to differentiated keratinocyte cultured cells (LDKs) to which ceramide NDS has not been added.

(Test Results 2-2)

Figure 4:
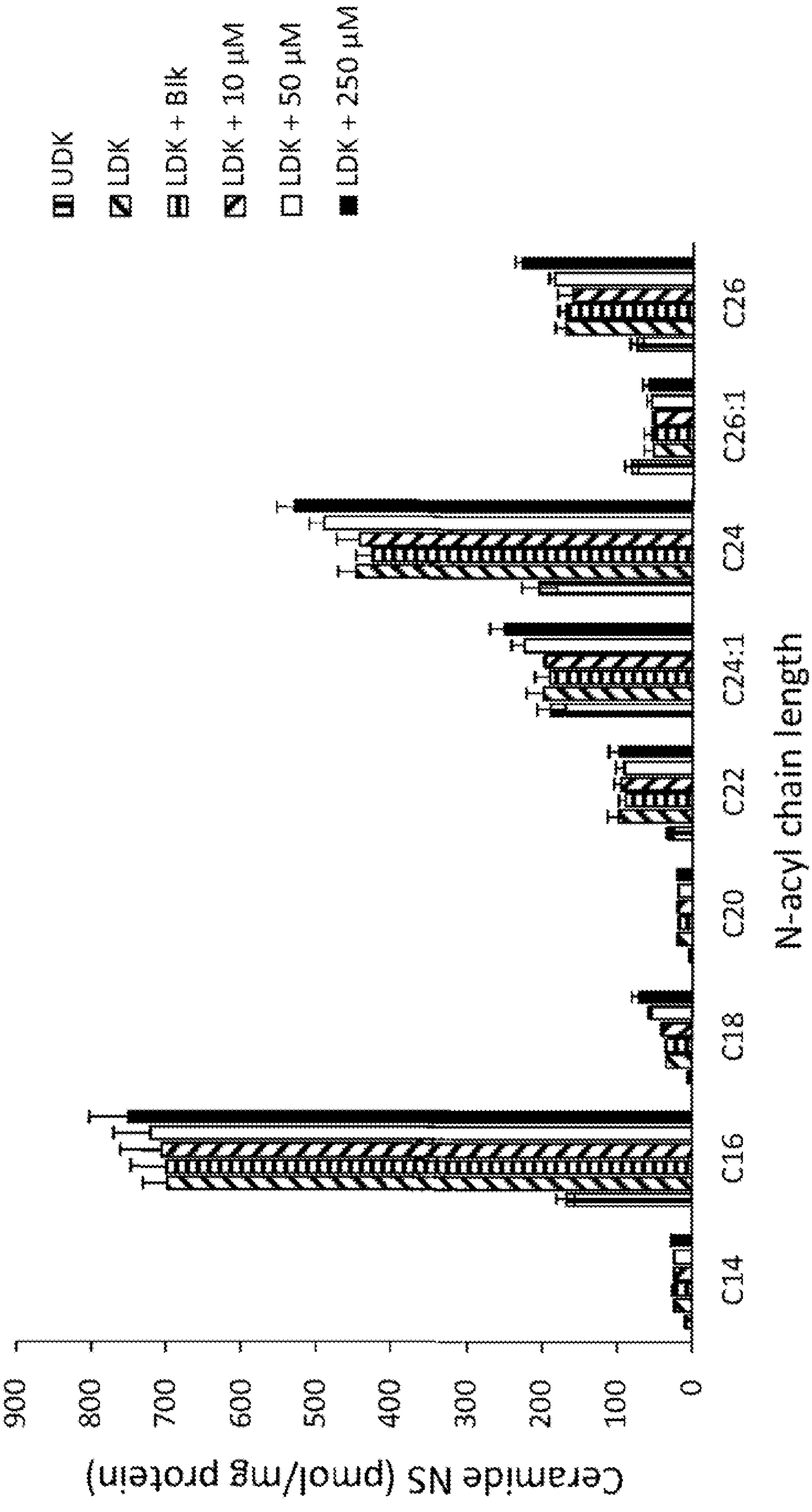
FIG. 4 is a diagram showing quantification results of ceramide NSs.

The quantification results of ceramide NSs are shown in FIG. 4.

As is clear from FIG. 4, it was confirmed that in the culture system to which ceramide NDS was added, the ceramide NSs having an amide bond having an acyl chain length of 14 to 26 and having a double bond at a 4-position of sphingosine base significantly increased. Note that # indicates a significant difference $p<0.01$ with respect to the differentiated cultured cells (LDK) to which ceramide NDS has not been added, and * indicates a significant difference $p<0.01$ with respect to the undifferentiated cells (UDK).

(Test Results 2 and 3)

Figure 5:
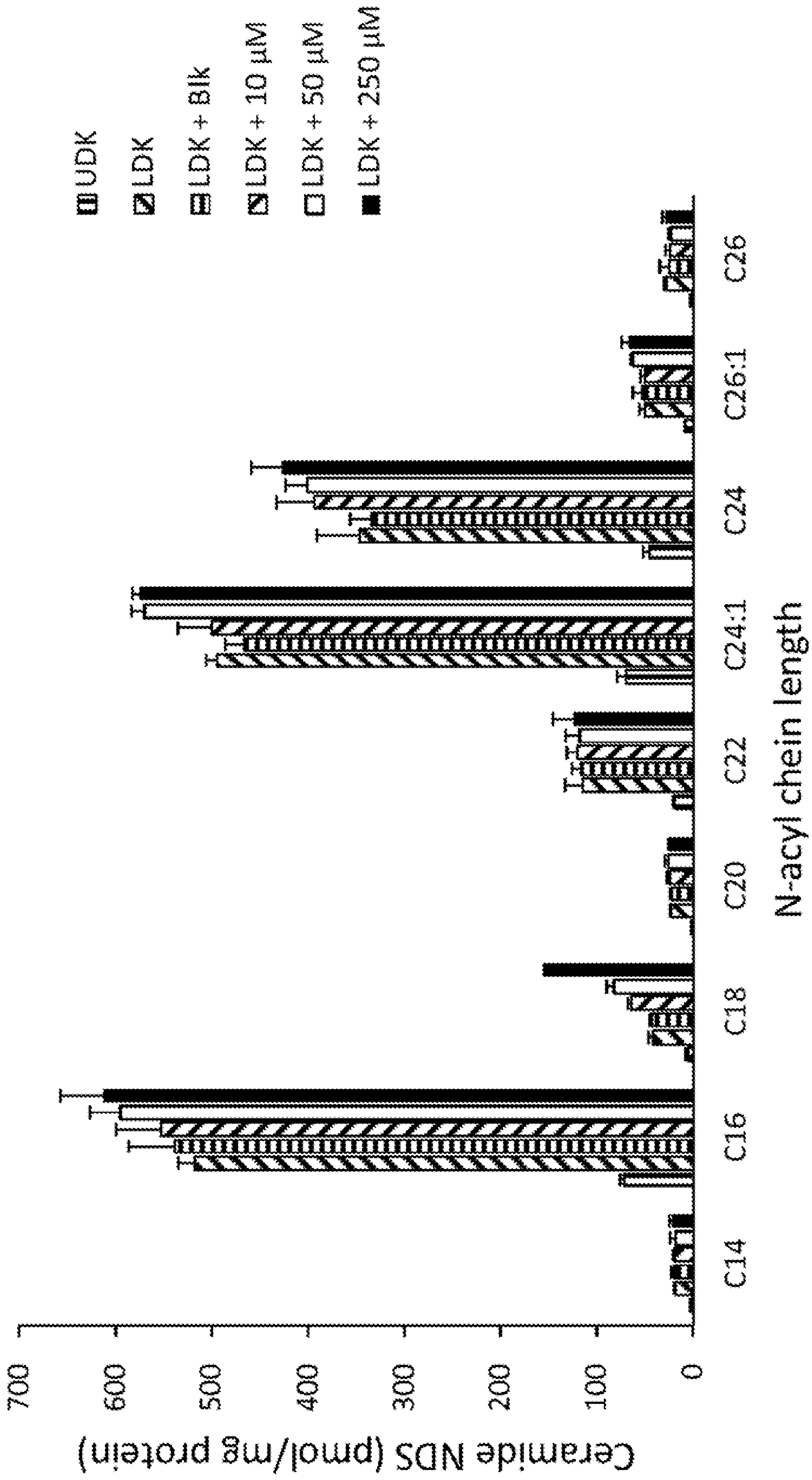
FIG. 5 is a diagram showing quantification results of ceramide NDSs.

The quantification results of ceramide NDSs are shown in FIG. 5.

As is clear from FIG. 5, it was confirmed that in the culture system to which ceramide NDS was added, ceramide NDSs having different acyl chain lengths of 14 to 26 significantly increased. Note that # indicates a significant difference $p<0.01$ with respect to the differentiated cultured cells (LDK) to which ceramide NDS has not been added, and * indicates a significant difference $p<0.01$ with respect to the undifferentiated cells (UDK).

From the above test results, it was revealed that by addition of a ceramide preparation containing ceramide NDS (acyl chain length C18), not only ceramide NDS having different acyl chain lengths but also various ceramide species such as ceramide NS and ceramide EOS are grown.

In the ceramide NP preparation prepared in Comparative Example 2, there was no tendency that various ceramide species were significantly grown.

Example 4

According to a common method, 100 g of a ceramide growth skin lotion containing 0.1 mass % of ceramide NDS was produced in accordance with the formulation shown in the following table (unit: mass %, in the table).

TABLE 3

| | |
|---|---|
| Concentrated glycerin | 3.00 |
| 1,3-butylene glycol | 5.00 |
| Paraoxybenzoic acid ester | 0.20 |
| Fragrance | 0.01 |
| Ceramide composition of Example 1 | 10.00 |
| Purified water | to 100.00 |

Example 5

According to a common method, 100 g of a ceramide growth serum containing 0.25 mass % of ceramide NDS was produced in accordance with the formulation shown in the following table (unit: mass %, in the table).

TABLE 4

| | |
|---|---|
| Hydroxyethyl cellulose | 0.50 |
| Concentrated glycerin | 5.00 |
| 1,3-butylene glycol | 5.00 |
| Paraoxybenzoic acid ester | 0.20 |
| Fragrance | 0.01 |
| Ceramide composition of Example 1 | 25.00 |
| Purified water | to 100.00 |

Example 6

According to a common method, 100 g of a ceramide growth emollient cream containing 0.05 mass % of ceramide NDS was produced in accordance with the formulation shown in the following table (unit: mass/a, in the table).

TABLE 5

| | |
|---|---|
| Hydrogenated oil | 6.00 |
| Stearic acid | 3.00 |
| Cetanol | 4.00 |
| Squalene | 2.00 |
| Neopentylglycol dicaprate | 8.00 |
| Polyoxyethylene sorbitan monostearate (20E.O.) | 4.00 |
| Lipophilic glycerin monostearate | 2.30 |
| Stearoyl N-methyl taurine sodium | 1.70 |
| Concentrated glycerin | 1.00 |
| 1,3-butylene glycol | 7.00 |
| Concentrated glycerin | 3.00 |
| Paraoxybenzoic acid ester | 0.25 |
| Fragrance | 0.05 |
| Ceramide composition of Example 1 | 5.00 |
| Purified water | to 100.00 |

Example 7

According to a common method, 100 g of a ceramide growth emollient milk containing 0.05 mass % of ceramide NDS was produced in accordance with the formulation shown in the following table (unit: mass %, in the table).

TABLE 6

| | | |
|---|---|---|
| Stearic acid | | 1.00 |
| Cholesteryl isostearate | | 2.00 |
| Jojoba oil | | 4.00 |
| Squalene | | 8.00 |
| Sorbitan sesquioleate | | 0.80 |
| Polyoxyethylene sorbitan monostearate (20E.O.) | | 1.20 |
| 1.3-butylene glycol | | 5.00 |
| Paraoxybenzoic acid ester | | 0.25 |
| L-arginine | | 0.40 |
| Carboxyvinyl polymer | | 0.20 |
| Fragrance | | 0.05 |
| Ceramide composition of Example 1 | | 5.00 |
| Purified water | to | 100.00 |

Example 8

According to a common method, 100 g of a ceramide growth conditioning shampoo containing 0.05 mass % of ceramide NDS was produced in accordance with the formulation shown in the following table (unit: mass %, in the table).

TABLE 7

| | | |
|---|---|---|
| Polyoxyethylene laureth ether sodium sulfate | | 14.00 |
| Amidopropyl betaine laurate | | 4.00 |
| Coconut oil fatty acid diethanolamide | | 3.00 |
| Cationized cellulose | | 0.50 |
| Ethylene glycol distearate | | 1.00 |
| Paraoxybenzoic acid ester | | 0.25 |
| Citric acid | Qs | |
| Fragrance | | 0.50 |
| Ceramide composition of Example 1 | | 5.00 |
| Purified water | to | 100.00 |

Example 9

According to a common method, 100 g of a ceramide growth hair rinse containing 0.05 mass % of ceramide NDS was produced according to the formulation shown in the following table (unit: mass %, in the table).

TABLE 8

| | | |
|---|---|---|
| Stearyl trimethylammonium chloride | | 1.00 |
| Cetanol | | 3.00 |
| Methylpolysiloxane | | 1.00 |
| Polyoxyetylene stearyl ether | | 1.00 |
| Propylene glycol | | 5.00 |
| Paraoxybenzoic acid ester | | 0.25 |
| Sodium hydroxide | Qs | |
| Citric acid | Qs | |
| Fragrance | | 0.50 |
| Ceramide composition of Example 1 | | 5.00 |
| Purified water | to | 100.00 |

Example 10

According to a common method, 100 g of a ceramide growth hair conditioner containing 0.05 mass % of ceramide NDS was produced in accordance with the formulation shown in the following table (unit: mass %, in the table).

TABLE 9

| | | |
|---|---|---|
| Stearyl trimethylammonium chloride | | 0.50 |
| Distearyl dimethylammonium chloride | | 1.50 |
| Jojoba oil | | 2.50 |
| Cetanol | | 4.50 |
| Liquid lanolin | | 2.00 |
| Polyoxyetylene stearyl ether | | 1.50 |
| Concentrated glycerin | | 7.00 |
| Paraoxybenzoic acid ester | | 0.25 |
| Sodium hydroxide | Qs | |
| Citric acid | Qs | |
| Fragrance | | 0.50 |
| Ceramide composition of Example 1 | | 5.00 |
| Purified water | to | 100.00 |

Example 11

According to a common method, 100 g of a ceramide growth hair tonic containing 0.05 mass % of ceramide NDS was produced in accordance with the formulation shown in the following table (unit: mass %, in the table).

TABLE 10

| | | |
|---|---|---|
| Swertia japonica extract | | 2.00 |
| L-Menthol | | 0.10 |
| Hinokitiol | | 0.01 |
| Fragrance | | 0.10 |
| Paraoxybenzoic acid ester | | 0.20 |
| Polyoxyethylene hydrogenated castor oil | | 0.50 |
| Ceramide composition of Example 1 | | 5.00 |
| Purified water | to | 100.00 |

Example 12

According to a common method, 100 g of a ceramide growth liquid bath agent containing 0.05 mass % of ceramide NDS was produced in accordance with the formulation shown in the following table (unit: mass %, in the table).

TABLE 11

| | | |
|---|---|---|
| Dipropylene glycol | | 50.00 |
| 1,3-butylene glycol | | 10.00 |
| Paraoxybenzoic acid ester | | 0.20 |
| Fragrance | | 1.00 |
| Ceramide composition of Example 1 | | 5.00 |
| Purified water | to | 100.00 |

Although the present invention has been described in detail using specific embodiments, it will be apparent to those skilled in the art that various modifications and variations are possible without departing from the spirit and scope of the present invention. The present application is based on a Japanese Patent Application (Japanese Patent Application No. 2020-40142) filed on Mar. 9, 2020, contents of which are incorporated herein by reference.

The invention claimed is:

1. A method for promoting biosynthesis of two or more ceramide species selected from the group consisting of ceramide EOS, ceramide NS and a first ceramide NDS in a skin stratum corneum, the method comprising:

topically applying a ceramide growth promoting agent on skin of a human subject in need thereof, thereby promoting the biosynthesis of the ceramide species wherein said ceramide growth promoting agent comprises a second ceramide NDS in an amount of 0.01 mass % to 5 mass % based on a total amount of the ceramide growth promoting agent.

2. The method according to claim 1, wherein the ceramide growth promoting agent further comprises any one or more of cholesterol, phytosterol, polyglycerin fatty acid ester, and polyhydric alcohol.

3. The method according to claim 1, wherein the ceramide growth promoting agent further comprises water and any one or more of cholesterol, decaglycerol monostearate, butylene glycol, and glycerin.

4. The method according to claim 1, wherein the second ceramide NDS in the ceramide growth promoting agent is (2S,3R)-2-octadecanoylaminooctadecane-1,3-diol.

5. The method according to claim 1, wherein the second ceramide NDS in the ceramide growth promoting agent is in a form of dispersed particles having a diameter of 0.45 μm or less, and wherein the ceramide growth promoting agent is free of a fatty acid and/or a phospholipid and all components in the ceramide growth promoting agent are nonionic.

6. A skin cosmetic, a skin protective agent, a lip care preparation, a skin cleanser, or a bath agent, comprising a ceramide growth promoting agent, wherein the ceramide growth promoting agent comprises ceramide NDS in an amount of 0.01 mass % to 5 mass % based on a total amount of the ceramide growth promoting agent, wherein the ceramide NDS in the ceramide growth promoting agent is in a form of dispersed particles having a diameter of 0.45 μm or less, wherein the ceramide growth promoting agent is free of a fatty acid and/or a phospholipid and all components in the ceramide growth promoting agent are nonionic, and wherein the ceramide NDS in the ceramide growth promoting agent has an acyl chain length of C18, and wherein, upon topical application of the ceramide growth promoting agent on skin of a human subject, ceramide NDSs having acyl chain lengths of C14, C16, C20, C22, C24, and C26 are increased within skin stratum corneum.

* * * * *